(12) United States Patent
Williams et al.

(10) Patent No.: US 8,241,680 B2
(45) Date of Patent: Aug. 14, 2012

(54) NUTRACEUTICAL PRODUCT CONTAINING ANATABINE AND YERBA MATÉ

(75) Inventors: Jonnie R. Williams, Manakin-Sabot, VA (US); Curtis Wright, Gloucester, MA (US)

(73) Assignee: Rock Creek Pharmaceuticals, Inc., Gloucester, MA (US)

( * ) Notice: Subject to any disclaimer, the term of this patent is extended or adjusted under 35 U.S.C. 154(b) by 30 days.

(21) Appl. No.: 12/826,985

(22) Filed: Jun. 30, 2010

(65) Prior Publication Data

US 2012/0003341 A1    Jan. 5, 2012

(51) Int. Cl.
*A01N 65/38* (2009.01)
*A01N 65/00* (2009.01)
*C07D 401/04* (2006.01)
*A24B 15/00* (2006.01)

(52) U.S. Cl. ...... 424/751; 131/352; 424/769; 546/279.4
(58) Field of Classification Search .................. None
See application file for complete search history.

(56) References Cited

U.S. PATENT DOCUMENTS

| | | | |
|---|---|---|---|
| 2,930,720 A | 3/1960 | Finberg | |
| 3,067,068 A | 12/1962 | Finberg | |
| 3,901,248 A | 8/1975 | Lichtneckert et al. | |
| 5,065,775 A | 11/1991 | Fagg | |
| 5,119,835 A | 6/1992 | Heemann et al. | |
| 5,387,416 A | 2/1995 | White et al. | |
| 5,512,306 A | 4/1996 | Carlsson et al. | |
| 5,525,351 A | 6/1996 | Dam | |
| 5,573,774 A | 11/1996 | Keenan | |
| 5,582,837 A | 12/1996 | Shell | |
| 5,760,049 A | 6/1998 | Viner | |
| 5,845,647 A | 12/1998 | O'Donnell, Jr. et al. | |
| 5,942,244 A | 8/1999 | Friedman et al. | |
| 5,945,107 A * | 8/1999 | Hessel et al. ................. | 424/728 |
| 5,972,389 A | 10/1999 | Shell et al. | |
| 6,090,411 A | 7/2000 | Pillay et al. | |
| 6,166,032 A | 12/2000 | Viner | |
| 6,202,649 B1 | 3/2001 | Williams | |
| 6,210,710 B1 | 4/2001 | Skinner | |
| 6,217,903 B1 | 4/2001 | Skinner | |
| 6,311,695 B1 | 11/2001 | Williams | |
| 6,350,479 B1 | 2/2002 | Williams et al. | |
| 6,497,234 B1 | 12/2002 | Coy-Herbert | |
| 6,534,527 B2 | 3/2003 | Wolfson et al. | |
| 6,569,470 B2 | 5/2003 | Williams et al. | |
| 6,582,737 B2 | 6/2003 | Hirsh et al. | |
| 6,723,340 B2 | 4/2004 | Gusler et al. | |
| 7,115,285 B2 | 10/2006 | McKee et al. | |
| 7,279,184 B2 | 10/2007 | Gow et al. | |
| 7,294,353 B2 | 11/2007 | Gow et al. | |
| 7,329,419 B2 | 2/2008 | Yatcilla et al. | |
| 6,929,811 B2 | 10/2010 | Williams et al. | |
| 2002/0025300 A1 | 2/2002 | Wolfson et al. | |
| 2002/0054926 A1 * | 5/2002 | Williams et al. ............ | 424/751 |
| 2004/0013752 A1 | 1/2004 | Wolfson | |
| 2004/0198754 A1 | 10/2004 | McKee et al. | |
| 2005/0061339 A1 | 3/2005 | Hansson et al. | |
| 2005/0176777 A1 | 8/2005 | Williams et al. | |
| 2010/0154810 A1 | 6/2010 | Williams | |

FOREIGN PATENT DOCUMENTS

EP    1338211 A1 *  8/2003
WO   WO 9842209 A1 * 10/1998

OTHER PUBLICATIONS

Heck and de Mejia, "Yerba Mate Tea (Ilex paraguariensis): a Comprehensive Review of Chemistry, Health Implications, and Technological Considerations," J. Food Sci. Nov. 2007;72(9):R138-51.
International Search Report for PCT/US2011/040309 mailed Feb. 17, 2012.
Manuella Lanzetti, R.D. et al., Mate tea reduced acute lung inflammation in mice exposed to cigarette smoke, Nutrition, Feb. 2008, Vol. 24, pp. 375-381.

* cited by examiner

*Primary Examiner* — Chris R Tate
*Assistant Examiner* — Russell Fiebig
(74) *Attorney, Agent, or Firm* — Banner & Witcoff, Ltd.

(57) ABSTRACT

Nutraceutical compositions containing anatabine and Yerba maté extract are efficacious for temporarily reducing the desire to smoke, reducing nicotine cravings, the treatment of smoking cessation, tobacco withdrawal symptoms, tobacco dependence, weight loss, and/or related disorders.

20 Claims, 3 Drawing Sheets

NUTRACEUTICAL PRODUCT CONTAINING ANATABINE AND YERBA MATÉ

BACKGROUND

Tobacco is among the most chemically complex substances known, with tobacco and tobacco smoke containing more than 8,000 compounds. While nicotine is regarded as the principal addictive component in tobacco, a variety of other factors also are believed to contribute to tobacco addiction. For example, tobacco smoke has been reported to have a monoamine oxidase (MAO) inhibitory effect. MAO is an enzyme involved in the breakdown of dopamine, which is a pleasure-enhancing neurotransmitter. See J. S. Fowler et al., "Inhibition of Monoamine Oxidase B in the Brain of Smokers," Nature (Lond), 379(6567):733-736 (1996); J. Stephenson, "Clues Found to Tobacco Addiction," Journal of the American Medical Association, 275(16): 1217-1218 (1996).

In addition to nicotine, tobacco also contains the minor alkaloids nornicotine, anabasine, and anatabine. High doses of tobacco alkaloids are known to cause disadvantageous side effects. Nicotinic alkaloids have been reported to cause nausea, dizziness, gastrointestinal distress, and palpitations in high doses. Goodman and Gilman, The Pharmacological Basis of Therapeutics, $11^{th}$ Ed., pp. 232-233.

Yerba maté is a beverage common in South America where it is consumed for its stimulatory effects. Yerba maté is made from the stems and leaves of *Ilex paraguarensis*, a member of the Holly family, Aquifoliaceae. The mate beverage is usually prepared by one or more additions of boiling water to the dried plant material. The repeated additions of boiled water extract the stimulants from the plant. Numerous bioactive molecules are found in Yerba maté. Maté's stimulant affect has been attributed to methylxanthines released by the preparation process. Methylxanthines present in Yerba maté include caffeine, theobromine, theophylline and caffeoyl derivatives such as chlorogenic acid and caffeic acid. Caffeine is considered the principal stimulant. However, consumption of caffeine with other Yerba maté stimulants can give rise to undesirable side effects, commonly referred to as "xanthine toxicity," which is characterized by palpitations, nausea, urinary dysfunction and visual disturbances. Goodman and Gilman, The Pharmacological Basis of Therapeutics, $11^{th}$ Ed., pp. 728-729.

Nicotine replacement therapy (NRT) has become one of the most widely used techniques for treating smoking cessation. Some smoking cessation aids deliver nicotine via transdermal or transmucosal devices, which allow delivery of nicotine through the skin or mouth, respectively. U.S. Pat. No. 5,512,306 describes a smoking cessation aid in the form of an inclusion complex formed between nicotine and a cyclo compound such as polysaccharide. U.S. Pat. No. 5,525,351 discloses a saliva-soluble stimulant formed from a gel and nicotine.

Nicotine replacement therapy has had limited success in the treatment of cigarette addiction and as a means of reducing the level of consumption of cigarettes. Two of the significant disadvantages of NRT are, first, the therapy involves administering nicotine, a toxic and addictive substance. Second, many individuals who use tobacco, particularly smokers, experience an unpleasant taste (or "burn") when ingesting nicotine orally. Smokers also experience similar effects from using smokeless tobacco products and, as a result, their use as an alternative to cigarettes has met with limited success. It would be desirable to develop a non-nicotine product that would avoid the addictive attributes of nicotine as well as the unpleasant taste associated with consumption of nicotine-containing products and which would provide temporary relief from the desire to smoke.

SUMMARY

Embodiments of the present invention are directed to combinations of substances for temporarily reducing the desire to smoke and, in other contexts, tobacco withdrawal symptoms, tobacco dependence, weight loss, and/or other related disorders. More particularly, embodiments of the present invention are directed to compositions containing anatabine and Yerba maté extract in amounts generally found in naturally occurring foodstuffs and beverages to provide temporary relief from the craving for a cigarette or for assistance in maintaining a healthy metabolism. According to aspects of the present invention, the compositions are referred to a "nutraceuticals" insofar as the ingredients of the compositions are obtained from or found in foodstuffs and/or beverages and in amounts generally found in naturally occurring foodstuffs and/or beverages. The ingredients can be obtained from or otherwise derived or extracted from foodstuffs or they can be synthetically prepared. For example, anatabine may be prepared synthetically or may be provided in the form of an anatabine-containing plant extract.

Nutraceutical products containing relatively small levels of anatabine and Yerba maté (e.g., levels on par with those found in certain food products) were unexpectedly found to be effective for temporarily reducing cravings for tobacco. High doses of anatabine and Yerba maté individually have been reported as exhibiting MAO inhibition activity. However, embodiments of the present invention are based on the surprising discovery that compositions containing both components in amounts well below what would be regarded as MAO inhibitory levels are efficacious for the temporary reduction of tobacco cravings and, in certain contexts, for smoking cessation, tobacco withdrawal symptoms, tobacco dependence, and weight loss.

BRIEF DESCRIPTION OF THE DRAWINGS

A more complete understanding of the present invention and certain advantages thereof may be acquired by referring to the following detailed description in consideration with the accompanying drawings, in which.

DETAILED DESCRIPTION

Figure 1:
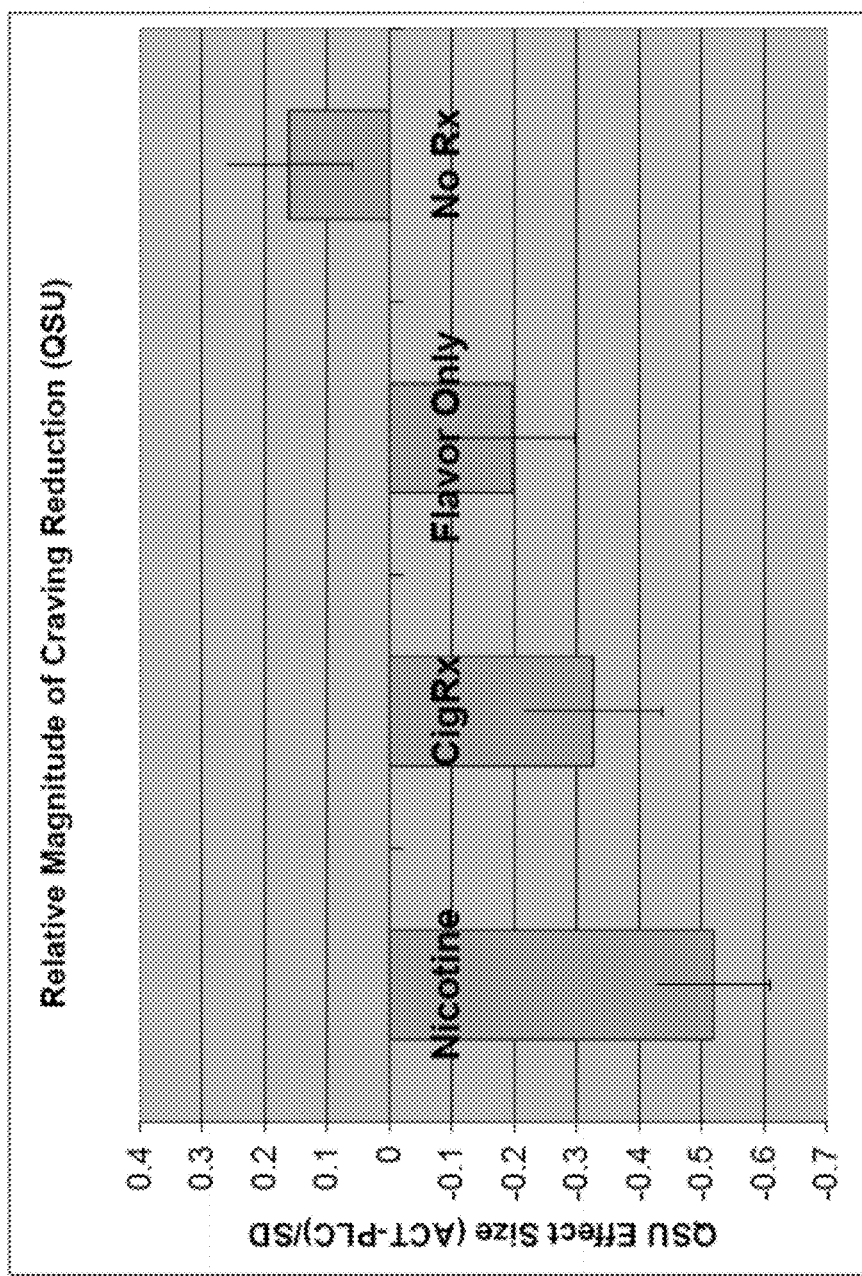
FIG. 1 is a graph showing the relative magnitude of craving reduction (QSU) upon administration of tobacco (Nicotine), anatabine/Yerba maté (CigRx™), flavor-only, and no treatment (No Product)

It has been found that compositions combining Yerba maté extracts and anatabine are effective for the temporary reduction in cravings for tobacco products, and alleviation of tobacco withdrawal symptoms, while minimizing undesirable side effects associated with the administration of either Yerba maté or anatabine alone, or with nicotine replacement therapy or the use of smokeless tobacco products.

In a first embodiment, a composition comprises a Yerba maté extract, synthetic anatabine, and a pharmaceutically acceptable vehicle, diluent, or carrier.

In a second embodiment, a composition comprises a Yerba maté extract, an anatabine-containing plant extract, and a pharmaceutically acceptable vehicle, diluent, or carrier.

In a further embodiment, a method is provided for administering to a subject a composition containing Yerba maté extract and anatabine for the temporary reduction of tobacco cravings and, in certain contexts, for smoking cessation, tobacco withdrawal symptoms, tobacco dependence, and weight loss.

The compositions may be prepared in a variety of formulations. For example, the compositions may be in the form of a beverage, a chew, a tablet, a lozenge, or a gum. The compositions alternatively may be in the form of chewing tobaccos, snuffs, snus, and the like. Additional inactive ingredients may be added to improve taste or stability. Optionally, other components such as sweetening and flavoring agents may be added.

Optionally, the compositions may be provided in a time-release formulation to provide therapeutic effects over extended periods. Extended release formulations are known in the art. For example, swellable particles are taught in U.S. Pat. Nos. 5,582,837, 5,972,389, and 6,723,340. Polymer matrices are taught in U.S. Pat. Nos. 6,210,710, 6,217,903, and 6,090,411. Typical materials used for extended release formulations are the polymers poly(ethylene oxide) and hydroxypropyl methylcellulose. Tablet formulations for slow release are also described in U.S. Pat. No. 5,942,244.

Anatabine may be obtained from any suitable source, either as an extract or as synthesized anatabine. Synthetic anatabine is commercially available from several chemical suppliers. Anatabine may be prepared synthetically, such as via a benzophenoneimine pathway as described in co-pending application Ser. No. 12/729,346, filed Mar. 23, 2010, the disclosure of which is incorporated herein by reference in its entirety. Alternatively, anatabine may be obtained by extraction from tobacco or other plants, such as members of the Solanaceae family, such as datura, mandrake, belladonna, capsicum, potato, nicotiana, eggplant, and petunia.

In Step 1 of the synthesis described in co-pending application Ser. No. 12/729,346, 3-aminomethylpyridine is reacted with benzophenoneimine (or benzophenoneimine substituted in either or both rings with nitrogen, a halogen, or an alkyl group) to form benzylhydrylidene-pyridin-3-ylmethyl-amine, also referred to herein as Formula I:

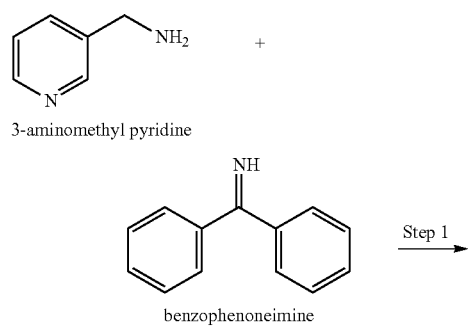

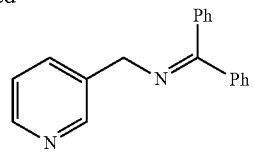

Formula I

Step 1 may be performed at any suitable temperature range. The reaction is exothermic, normally resulting in a temperature increase from ambient to about 45° C. to 55° C. If desired, the reaction mixture may be heated or cooled. In general, the rate of reaction increases at higher temperature and decreases at lower temperatures. For example, step 1 may be performed at about 30° C. to about 60° C. Most often, step 1 is performed at a temperature of about 45° C. to about 55° C.

The amount of time needed to complete Step 1 may vary depending on such factors such as reaction temperature and pressure. Normally, the reaction is completed in about 4 to about 9 hours, more usually from about 5 to about 7 hours.

Step 1 is particularly advantageous as it can be scaled up to facilitate larger scale production. For example, the amount of starting material (e.g. combined weight of 3-aminomethylpyridine and benzophenoneimine) used for a batch may be about 500 mg, about 1 g, about 5 g, about 10 g, about 20 g, about 25 g, about 30 g, about 40 g, about 50 g, about 100 g, about 200 g, about 500 g, about 1 kg, about 5 kg, or about 10 kg. Often, a medium scale synthesis starts with 20 g to 30 g of starting material. A large scale synthesis may start with 1 kg to 5 kg or more of starting material.

Using benzophenoneimine provides several key advantages over earlier methods and facilitates larger-scale synthesis as described above. First, the reaction by-product is ammonia rather than water. The ammonia escapes from the reaction mixture. By avoiding the presence of water as byproduct, the reaction temperature—50° C., for example—is much lower than the ~85° C. used for the water-removing benzene reflux step in the method of Deo et al. Using lower temperatures in the preparation of the compound offers improved economic and environmental efficiencies. Also, by omitting benzene from the reaction, the synthesis is safer and more environmentally-friendly. Avoiding the presence of water is also beneficial in terms of improved product stability because anatabine is moisture-sensitive.

Second, because benzophenoneimine is liquid, Step 1 may proceed in a solvent-less reaction medium such that the purity of the isolated intermediate is enhanced and avoids the need for a workup reaction. Purity of Formula I compound typically is about 93-95% whereas the Deo et al. method yields only about 83-85% purity of the intermediate.

The purity of Formula I compound may be as high as about 100%, about 99%, about 98%, about 97%, about 96%, about 95%, about 94%, or about 93%. Often, the Formula I compound is about 93% to about 95% pure.

In step 2i, the compound of Formula I is reacted with a non-nucleophilic base, such as lithium diisopropylamide (LDA), and a dielectrophile, such as cis-1,4-dichloro-2-butene to form a compound of Formula II. The non-nucleophilic base typically is added in a molar excess, for example, at about 1.2 equivalents (eq), about 1.3 eq, about 1.4 eq, about 1.5 eq, about 1.6 eq, about 1.7 eq, about 1.8 eq, about 1.9 eq, or about 2.0 eq. Often the non-nucleophilic base is added in an amount of about 1.3 eq to about 1.7 eq, more usually from about 1.4 to about 1.6 eq.

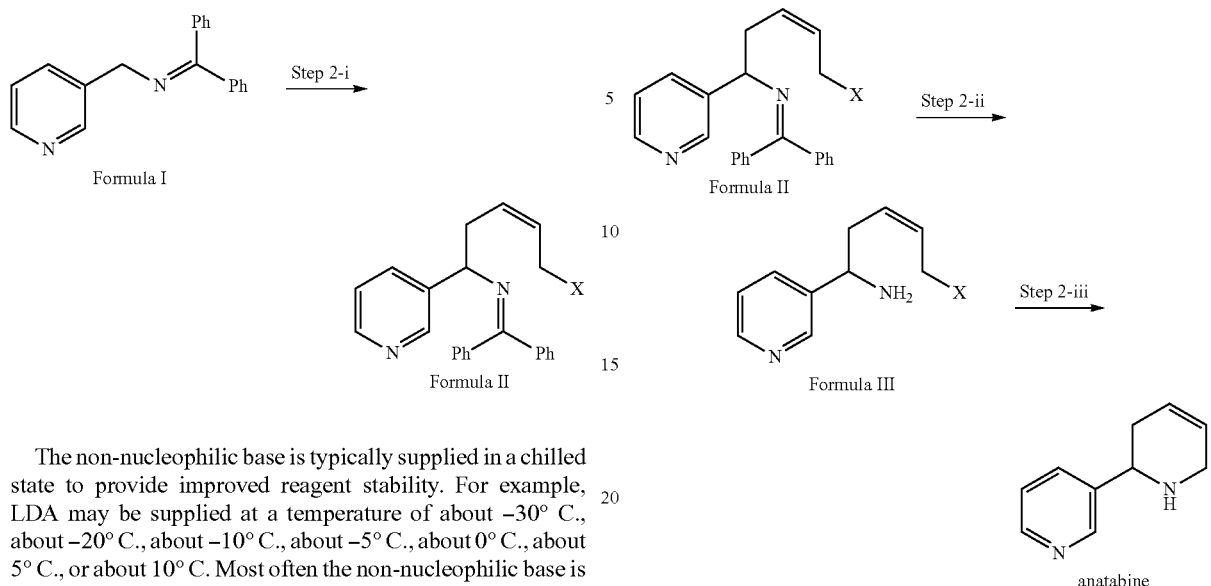

Formula I
Formula II
Formula III
anatabine

The non-nucleophilic base is typically supplied in a chilled state to provide improved reagent stability. For example, LDA may be supplied at a temperature of about −30° C., about −20° C., about −10° C., about −5° C., about 0° C., about 5° C., or about 10° C. Most often the non-nucleophilic base is provided at a temperature of about −30° C. to about 0° C.

The Step 2i reaction may be incubated for a time suitable for the reaction to go to completion or substantial completion. For example, the reaction time for Step 2li often is about 10 minutes, about 20 minutes, about 30 minutes, about 40 minutes, about 50 minutes, or about 1 hour. Often, the reaction is incubated for about 20 to about 40 minutes.

As an alternative to LDA in step 2i, other strong bases such potassium tert butoxide (K'OBu) may be used. Potassium tert butoxide (K'OBu) was found to provide improved yield and purity. Using K'OBu we obtained an anatabine yield of 25% with 97% purity. Other alternatives to LDA include sodium hydride, sodamide, and other alkyllithium reagents.

Following addition of the non-nucleophilic base, a dielectrophile of Formula IV is added:

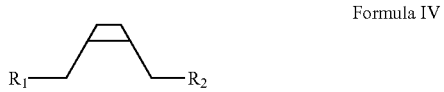

Formula IV wherein each of $R_1$ and $R_2$ is independently selected from the group consisting of chlorine, (Cl); bromine, (Br), and iodine, (I), tosylate, mesylate, and triflate. For example, $R_1$ and $R_2$ may both be Cl, such that the dielectrophile is cis-1,4-dichloro-2-butene. The dielectrophile may be added neat or in a suitable solvent, such as THF.

For step 2ii, Formula II compound is hydrolyzed with acid. Treatment with acid may be for any suitable time. For example, HCl (10%) treatment may be for about 5 minutes, about 10 minutes, about 20 minutes, about 30 minutes, or for about 1 hour. Often, acid treatment is for about 10 minutes to about 20 minutes. Other suitable acids include dilute sulfuric acid and phosphoric acid. For step 2iii, Formula III compound is basified, such as by treatment with solid $K_2CO_3$, then aqueous KOH solution (e.g., 40%) to achieve N-alkylation to yield anatabine. Other bases, such as Diaza(1,3)bicyclo [5.4.0]undecane (DBU), di-isopropyl ethylamine, or triethylamine, may also be used.

In another aspect, a method of recovering and purifying anatabine comprises extracting anatabine from the reaction product of Step 2iii using MTBE in a distillation process. The anatabine containing solution is basified to saturation with KOH and $K_2CO_3$. Addition of MTBE to the solution induces phase separation, with the anatabine separated into the organic phase, which provides an additional increase in anatabine purity. Subsequent distillation, followed by acid-base work up typically results in an anatabine purity of 99%.

Advantageously, this purification approach can be scaled up to industrial-scale manufacture. Purification by chromatography, which does not scale up from small-scale production, is avoided. Moreover, MTBE is more environmentally friendly than halogenated compounds such as chloroform. MTBE also improves extraction efficiency relative to halogenated compounds such as chloroform.

Anatabine prepared according to the methods disclosed herein displays good stability at a variety of temperatures. See, for example, Tables 3 and 4 in Examples 4 and 5, respectively. Purity of the anatabine may be retained for extended periods of time. For example, the anatabine may exhibit the indicated purity at 12 days, at 18 days, at 21 days, at 1 month, at 3 months, at 6 months, at 9 months, at 12 months at 18 months, at 24 months, and at 36 months, or longer. Further, anatabine remains stable when stored at a variety of temperatures. For example, the anatabine retains the indicated purity when stored at −20° C. to −10° C., −20° C. to 0° C., −10° C. to 0° C., 0° C. to 4° C., 2° C. to 8° C., 5° C. to 10° C., 10° C. to 15° C., 15° C. to 25° C., or 25° C. to 28° C. Stability is determined by any suitable art-recognized method. For example, anatabine stability may be monitored by high performance liquid chromatography (HPLC), liquid chromatography-mass spectroscopy (LC-MS), or nuclear magnetic resonance (NMR).

The synthesis described herein may yield significantly lower concentrations of byproducts, such as benzophenone, which can lower reaction yields and introduce impurities into the product. Concentrations of benzophenone, for example, are typically less than about 3% as compared to 8-12% that were found when reproducing the Deo et al. synthesis. Moreover, yield was 25% for the present invention but only 10% for the Deo et al synthesis.

In another aspect, acceptable pharmaceutical or food grade salts of anatabine are provided using an appropriate synthesis technique. Anatabine salts may provide improved chemical and chiral purity relative to the synthetic racemic alternative. Non-limiting examples of acceptable pharmaceutical or food grade salts that may be produced include tartrate, citrate, L-aspartate, camphor-10-sulphonate, cinnamate, cyclamate, fumarate, D-gluconate, L-glutamate, L-(+)-lactate, (±)-DL-lactate, maleate, malate, oxalate, galactarate, glucoheptonate, hippurate, malonate, (±)-DL-mandelate, nicotinate, salicylate, or succinate.

A tobacco extract may be prepared from cured tobacco stems, lamina, or both (hereinafter collectively referred to as "tobacco material"). In the extraction process, cured tobacco material is extracted with a solvent, typically water, ethanol, steam, or carbon dioxide. The resulting solution contains the soluble components of the tobacco, including alkaloids such as anatabine. In some examples, anatabine is purified from the other components of the tobacco using suitable techniques such as liquid chromatography. In other examples, the extract is used without further purification. The solution may then be dried and ground, as needed, to form a powder.

In some examples, the tobacco material is substantially denicotinized to remove a majority of other alkaloids such as nicotine, nornicotine, and anabasine. Denicotinizing is usually carried out prior to extraction of anatabine. Methods that may be used for denicotinizing tobacco materials are described, for example, in U.S. Pat. No. 5,119,835, the disclosure of which is hereby incorporated by reference. In general, tobacco alkaloids may be extracted from tobacco material with carbon dioxide under supercritical conditions. The tobacco alkaloids may then be separated from the carbon dioxide by dissolving an organic acid or a salt thereof, such as potassium monocitrate, in the carbon dioxide.

Flue (bright) varieties of tobacco are often used, i.e., Virginia flue. Other tobacco varieties may be used, such as Burley, dark-fired, and/or other commercial tobacco varieties. If desired, two or more tobacco varieties may be combined to form a blend. The powdered tobacco may be formed from cured tobacco stems, lamina, or both.

First, tobacco is grown and harvested. The tobacco is cured and then removed from the curing barn. If only the stem or lamina is being used, the stem or lamina may be separated from the rest of the leaf either before or after curing.

The tobacco may be cured using techniques designed to avoid or minimize the formation of carcinogenic tobacco-specific nitrosamines (TSNA). Such techniques are described, for example, in co-pending application Ser. No. 12/342,192, filed Dec. 23, 2008, and Williams U.S. Pat. No. 6,202,649, the disclosures of which are hereby incorporated by reference.

After curing, the tobacco material may be subjected to a sterilization technique. The sterilization technique typically irradiates the tobacco to destroy any microbes remaining on the tobacco. Any suitable radiation may be used such as, but not limited to, microwaves, gamma rays or electron beams, as described in U.S. Pat. No. 6,311,695.

Methods for forming aqueous tobacco extracts are known in the art as described, for example, in U.S. Pat. No. 5,065,775. In general, tobacco material is contacted with an aqueous solution to extract soluble components. The time of contact will depend on such factors as the water to tobacco ratio and the temperature of the aqueous solution. The aqueous extract produced by contact with the water solution is then separated from the insoluble fibrous tobacco residue, which can be accomplished using conventional solid-liquid separation techniques. For example, squeezing, centrifugation, and filtration techniques may be employed. If necessary, the separated tobacco extract may then be treated to adjust soluble solids content.

More particularly, cured tobacco material is contacted with an aqueous extraction solvent. Contact can be performed in either a continuous or batch-wise manner. The mixture of tobacco material and extraction solvent can be agitated in order to enhance removal of water-soluble components from the tobacco material. The mixture is subjected to separation conditions (e.g., using a centrifuge) so as to provide an aqueous tobacco extract (i.e., a water-soluble tobacco extract within the extraction solvent), and a water-insoluble tobacco residue.

The aqueous extraction solvent is primarily water, normally at least about 90 wt % water, and can be essentially pure water such as deionized water, distilled water, or tap water. The extraction solvent can be a co-solvent mixture, such as a mixture of water and one or more solvents that are miscible therewith. An example of such a co-solvent mixture is a solvent containing 95 parts water and 5 parts ethanol per 100 parts by weight. The extraction solvent also may include substances such as pH adjusters (i.e., acids or bases) or pH buffers dissolved therein. For example, an aqueous solvent can have ammonium hydroxide or gaseous ammonia incorporated therein so as to provide a solvent having a pH of about 8 or more.

The amount of the tobacco material which is contacted with the extraction solvent can vary over a wide range and depends upon such factors as the type of solvent, the temperature at which the extraction is performed, the type or form of tobacco material which is extracted, the manner in which contact of the tobacco material and solvent is conducted, and the type of extraction process which is performed. Typically, for a batch-wise extraction, the weight of extraction solvent relative to the tobacco stems is greater than about 6:1, oftentimes greater than about 8:1 and in certain instances can be greater than about 12:1. The manner for contacting the tobacco material with the extraction solvent is not particularly critical, e.g., the tobacco material can be extracted in either a continuous or batch-wise manner. For example, the tobacco material can be extracted using a continuous counter-current extractor.

Tobacco material can be extracted in a batch-wise manner one or more times using the solvent. Normally, the weight of extract and solvent relative to the weight of tobacco material for each batch extraction ranges from about 6:1 to about 40:1, more often from about 15:1 to 25:1. The number of times that the tobacco material is contacted batch-wise with the processed tobacco extract and solvent ranges from about 1 to about 8 times, more usually from about 3 to 5 times.

The tobacco material can be extracted continuously with water, ethanol, carbon dioxide, or steam as solvents. Normally, the weight of aqueous solvent relative to the tobacco material with which it is contacted during a continuous extraction process is greater than about 40:1 and often is greater than about 50:1. The conditions under which the extraction is performed can vary. Typical temperatures range from about −20 to 100° C., more often from about 10 to 60° C. Alternatively, steam can be used to extract the soluble components, which can be recovered in a condenser. The solvent/tobacco material mixture can be agitated (e.g., stirred, shaken or otherwise mixed) in order to increase the rate at which extraction occurs.

Typically, for a batch-wise extraction, adequate extraction of components occurs in less than about 60 minutes, oftentimes in less than about 30 minutes. A wide variety of components can be extracted from the tobacco material. Water-soluble tobacco components that are extracted from tobacco material using a solvent having an aqueous character include alkaloids (e.g., anatabine), acids, salts, sugars, and the like. Extracted tobacco components include many of the aroma-producing and flavorful substances of the tobacco material. As noted above, in some examples anatabine is isolated from the other components present in the tobacco, using suitable techniques such as chromatography.

The solvent and tobacco extract are separated from the insoluble tobacco residue. The manner of separation can vary; however, it is convenient to employ conventional separation techniques involving the use of filters, centrifuges, screw presses, converging belts, rotating disk presses, and the like. The insoluble residue can be treated to remove additional solvent and tobacco extract therefrom.

The solvent and tobacco components extracted thereby optionally can be filtered to remove suspended insoluble particles. In some cases it may be desirable to adjust the pH of the aqueous tobacco extract. For example, as described in U.S. Pat. No. 5,065,775, pH of an aqueous tobacco extract can be raised to promote removal of basic compounds, lowered to promote removal of acidic compounds, or made neutral to promote removal of neutral compounds. The tobacco extract usually contains from about 0.02 to about 0.08 milligrams of anatabine per gram of solution by weight. Liquid chromatography or other suitable techniques optionally may be used for further purification of anatabine.

After extraction, the aqueous extract may be dried into a powder by any suitable process, such as spray-drying. Spray-drying techniques are disclosed, for example, in U.S. Pat. No. 5,387,416, the disclosure of which is hereby incorporated by reference in its entirety. The powder may be bleached and then dried. The powder generally has a particle size of smaller than 80 mesh, and typically between 100 and 300 mesh. As will be appreciated by persons skilled in the art, a larger mesh number corresponds to a smaller particle size. A similar process may be utilized for synthetic anatabine.

If the average particle size of the powder is smaller than 80 mesh, as is typically the result with the extraction process, then the powder may be subjected to a process to increase its particle size, to conglomerate particles to make larger particles or both, to an average size greater than 80 mesh, preferably to an average particle size of between 14 and 80 mesh. Any suitable process may be used to increase particle size, such as by granulation or by rolling and grinding.

The powder may be granulated in any suitable manner. A preferred method uses a fluid bed granulator. The powder is placed in a fluid bed product bowl in the chamber of the fluid bed granulator. Air or other suitable gas is introduced into the chamber to blow the powder around the chamber. A liquid solution containing at least a binder is introduced into the chamber in the form of a very fine mist. The particles blow around in the mist. The particles become coated and start to clump together to make discrete uniform particles. A second mist of a buffer solution may then be introduced. After spraying, the particles are dried to the desired moisture level and lubricants may be added to the particles.

If desired, one or more flavorants may be added to the tobacco extract or anatabine, such as peppermint, menthol, and wintergreen or spearmint. Wintergreen oil, or methyl salicylate, can be prepared by heating methanol and salicylic acid in the presence of sulfuric acid, or by distillation from the leaves of *Gaultheria procumbens* or the bark of *Betula lenta*. If desired, one or more additional flavorants, such as propolis, eucalyptus, and/or cinnamon, may be provided to reduce irritation and to enhance the flavor of the powdered tobacco extract or anatabine. U.S. Pat. No. 5,845,647 describes the use of propolis in tobacco-containing chewing gum and other tobacco products. The amount of each flavorant typically ranges from about 0.5 to about 10 wt %, based on the total weight of the powdered tobacco.

Other ingredients may be added to the powder, such as sweeteners, fillers, coloring agents, buffers, and/or lubricants. Such ingredients may be added to the powdered tobacco extract or, if using a granulation process, to the binder solution. The relative amounts of such other components can vary over a wide range, depending on such factors as the particular tobacco extract used and consumer preferences. Typically, the amounts of individual components will range from about 0.5 wt % to about 10 wt %, based on the total weight of the powdered tobacco extract.

The composition may be prepared by any suitable technique and is not limited by any particular method for its production. For example, powdered tobacco extract or anatabine can be combined with excipients and a binder, and then granulated. The granulation can be dry-blended with the maté extract and any remaining ingredients, and compressed into a solid form such as a tablet.

The range of anatabine dose in the compositions may vary. Measured as mg/70 Kg body weight, the composition usually contains a dose of at least about 0.05 mg, and may contain about 0.1 mg, about 0.15 mg, about 0.2 mg, about 0.25 mg, or about 0.3 mg anatabine. The upper limit of the dose, measured as mg/70 Kg body weight, may be about 0.35 mg, about 0.4 mg, about 0.45 mg, about 0.5 mg, about 0.55 mg, or about 0.60 mg. Often, anatabine is present in a dose of about 0.1-0.3 mg/70 Kg body weight. The formulation may contain, for example, from about 0.1 to about 0.5 mg anatabine, and often contains from about 0.1 to about 0.3 mg or from about 0.1 to about 0.2 mg anatabine.

A suitable delivery system may be used to maximize the amount of anatabine released and ingested. For example, anatabine may be adsorbed on a cation exchange resin such as polymethacrilic acid (Amberlite IRP64 or Purolite C115HMR), as described in U.S. Pat. No. 3,901,248, the disclosure of which is hereby incorporated by reference in its entirety. Such cation exchange resins have been used commercially in nicotine replacement therapy, e.g., nicotine polacrilex.

The maté extract may be prepared by first drying leaves of the *Ilex paraguarensis* plant. Conventional techniques involving heating the leaves over a wood fire have been associated with the accumulation of carcinogenic polycyclic aromatic hydrocarbons (PAH). See, e.g., Heck and de Mejia, "Yerba Maté Tea (*Ilex paraguariensis*): a Comprehensive Review on Chemistry, Health Implications, and Technological Considerations," J Food Sci. 2007 November; 72(9): R138-51. Consequently, it is preferred that the *Ilex paraguarensis* leaves are dried in an environment that does not expose the leaves to combustion products, such as that described in Williams U.S. Pat. No. 6,202,649, to avoid the accumulation of PAH.

The dried leaves may then be subjected to extraction, using hot or cold water or a water/alcohol mixture, to remove the soluble components therefrom. The resulting extract contains the water-soluble (and/or alcohol-soluble) active components in the leaves. The amount of maté extract present in the composition may range, for example, from about 1 mg to about 100 mg, and usually ranges from about 1 mg to about 50 mg, often from about 10 to about 25 mg. Unless otherwise clear from context, amounts of maté extract described herein refer to the total amount of maté extract in milligrams.

Maté extract dose may be measured in caffeine equivalents. Caffeine equivalency can be determined by methods known in the art. The range of caffeine dose may vary over a wide range. For example, the lower limit of the dose, measured as mg caffeine equivalents/70 Kg body weight per day, may be about 1 mg, about 5 mg, about 10 mg, about 20 mg, about 30 mg, about 40 mg, about 50 mg, about 60 mg, about 70 mg, about 100 mg, or about 120 mg. The upper limit of the dose, measured as mg caffeine equivalents/70 Kg body weight per day may be about 140 mg, about 160 mg, about 180 mg, about 200 mg, about 220 mg, about 240 mg, about 260 mg, about 280 mg, or about 300 mg. Often, the range of daily dose in caffeine equivalents is about 1-100 mg, more usually from about 1-50 mg or from about 10-20 mg.

Combining particular amounts of synthetic anatabine (or tobacco extract) and maté extract was found to reduce cravings for smoking, while minimizing undesirable side effects associated with nicotine and other stimulants normally found in tobacco and Yerba maté. Thus, the jitteriness and exaggeration of nervousness associated with over-consumption of caffeine and the nausea and palpitations associated with anatabine are avoided while the benefits are retained. In some cases, the formulation may be administered as needed to satisfy cravings. Alternatively, a dosing regime may comprise administering the formulation at intervals such as once daily, twice daily, or three or more times daily, depending on such factors as the amount of active components in the formulation and the subject's physiological conditions.

The side effects associated with use of conventional tobacco and Yerba maté consumption prevent widespread adoption of their therapeutic use. It was a surprising discovery that nutraceutical compositions containing relatively low doses of anatabine and Yerba maté, e.g., levels lower than those which would be regarded as providing a MAO inhibitory effect, are nevertheless effective in reducing cravings for smoking, as discussed more fully in the examples below.

Further, by optimizing the beneficial stimulant effects while minimizing undesirable side effects, the compositions of the invention also may be useful in treating disorders that exhibit shaking symptoms such as Parkinson's Disease. For example, as Parkinson's disease progresses, shaking symptoms become more pronounced. However, by providing relatively low doses of anatabine and Yerba maté, the compositions of the invention advantageously avoid exacerbating any disease-induced shaking.

Example 1

Preparation of Synthetic Anatabine

Anatabine was prepared synthetically using 3-aminomethylpyridine and benzophenoneimine as starting materials, according to the procedures described below.

Step 1. Preparation of Formula I 3-aminomethylpyridine was added to neat benzophenoneimine (1 eq). The reaction was allowed to proceed for 6 hours at 50° C. providing Formula I as the product.

Example 2

Steps 2i to 2iii: Conversion of Formula I to Anatabine using Potassium Tert Butoxide (K$^t$OBu)

Step 2i: To Formula I of Example 1 was added K$^t$OBu (1.5 eq) in THF at −78° C. to −45° C. and the reaction was incubated for 30 min. Cis-1,4-dichloro-2-butene in 3 vol of THF at −78° C. was added, and the temperature was allowed to warm to −45° C. The reaction was allowed to proceed at −45° C. for 1-2 hours, providing Formula II. Optionally, the starting material may be added to the K$^t$OBu.

Step 2ii: 10% aqueous hydrochloric acid was added to the solution containing Formula II for 10-20 minutes to provide Formula III.

Step 2iii: The Formula III solution was basified by adding $K_2CO_3$ then treated with a 40% aqueous KOH solution to provide anatabine.

Results from different batches are show in Table 1.

TABLE 1

| Batch No. and amount | Reaction Conditions | Yield | Comments |
|---|---|---|---|
| A (2 g) | i) K$^t$OBu (1.1eq), THF, −78° C. to −45° C. for 30 min<br>ii) cis-1,4-dichloro-2-butene −45° C. for 1-2 h<br>iii) 10% aq HCl, 10-20 min, ether wash.<br>iv) $K_2CO_3$, 40% aqueous KOH | 0.7 g (crude) | SM was added to K$^t$OBu. 64.52% of Step 2i product Anatabine 65.12% pure by HPLC |
| B (2 g) | i) K$^t$OBu (1.5eq), THF, −78° C. to −45° C. for 30 min<br>ii) cis-1,4-dichloro-2-butene −45° C. for 1-2 h<br>iii) 10% aq HCl, 10-20 min, ether wash.<br>iv) $K_2CO_3$, 40% aqueous KOH | 0.68 g (crude) | Note that 1.5 eq of K$^t$OBu was used. 70.32% of Step 2i product Anatabine 67.06% pure by HPLC |
| C (25 g) | i) K$^t$OBu (1.1eq), THF, −78° C. to −45° C. for 30 min<br>ii) cis-1,4-dichloro-2-butene −45° C. for 1-2 h<br>iii) 10% aq HCl, 10-20 min, ether wash.<br>iv) $K_2CO_3$, 40% aqueous KOH | 8.5 g (crude) | 50% of Step 2i product Anatabine 57.7% pure by HPLC |

Example 3

Steps 2i to 2iii alternate route: Conversion of Formula I to Anatabine using LDA Formula I was prepared according to Example 1. LDA was added to Formula I at −10 to 0° C. Cis-1,4-dichloro-2-butene was added at −78° C. to −45° C. Steps 2 ii and 2 iii were performed according to Example 2.

TABLE 2

| Batch No. and amount | Reaction Conditions | Yield | Comments |
|---|---|---|---|
| D (25 g) | i) LDA (1.2eq), THF, −30° C. to 0° C. for 30 min<br>ii) cis-1,4-dichloro-2-butene −78° C. to −45° C. for 1-2 h<br>iii) 10% aq HCl, 10-20 min, ether wash.<br>iv) $K_2CO_3$, 40% aqueous KOH | 6.9 g (crude) | 71% conversion in IPC. 23.14% SM was seen in Step 2i. 72.64% purity by HPLC. |
| E (5 g) | i) LDA (1.5eq) −30° C. to 0° C. for 30 min<br>ii) cis-1,4-dichloro-2-butene −78° C. to −45° C. for 1-2 h<br>iii) 10% aq HCl, 10-20 min, ether wash.<br>iv) $K_2CO_3$, 40% aqueous KOH | — | 80% conversion in IPC Anatabine 70.6% pure by HPLC |
| F (25 g) | i) LDA (2.0eq), −30° C. to 0° C. for 30 min<br>ii) cis-1,4-dichloro-2- | — | 67% conversion in IPC Anatabine 76.1% pure |

TABLE 2-continued

| Batch No. and amount | Reaction Conditions | Yield | Comments |
|---|---|---|---|
| | butene −78° C. to −45° C. for 1-2 h<br>iii) 10% aq HCl, 10-20 min, ether wash.<br>iv) $K_2CO_3$, 40% aqueous KOH | | by HPLC |
| G (25 g) | i) LDA (1.5eq), −30° C. to 0° C. for 30 min<br>ii) cis-1,4-dichloro-2-butene −78° C. to −45° C. for 1-2 h<br>iii) 10% aq HCl, 10-20 min, ether wash.<br>iv) $K_2CO_3$, 40% aqueous KOH | | Anatabine 73.7% pure by HPLC |

Example 3a

Recovery/Purification of Anatabine Using MTBE and Distillation

The product of Example 2, Step 2iii was extracted with methyl t-butyl ether (MTBE), followed by distillation of the solvent and product distillation using a glass distillation assembly. Optionally, for scale-up, wiped film or thin film evaporation may be used. Yield of step 2 was 40%; overall yield was 26%.

Comparative Example 3a

Recovery/Purification of Anatabine Using Chloroform Column Chromatography

The product of Step 2iii was treated with chloroform extraction as described in Deo et al. Chloroform extraction resulted in an anatabine yield of 10%.

Example 4

Stability Analysis of Formula I

Several batches of Formula I produced by reacting benzophenoneimine with aminomethylpyridine in the absence of benzene were stored refrigerated and also at room temperature. Testing by HPLC shows that purity was constant when refrigerated and only deviated 1-2% at room temperature.

TABLE 3

| Days | Purity (%) (stored at 2-8° C.) | Purity (%) (stored at 25-28° C.) |
|---|---|---|
| 1 | 88.61 | 88.93 |
| 2 | 88.83 | 85.49 |
| 3 | 88.30 | 88.02 |
| 6 | 88.83 | 86.62 |
| 12 | 88.75 | 87.47 |
| 18 | 88.46 | 87.25 |

Example 5

Stability Analysis of Anatabine Base With and Without BHT as a Preservative

Anatabine base stability was analyzed with and without BHT (3,5-di-tert-butyl-4-hydroxytoluene). The initial purity of BHT-free anatabine base was 94.95%. The initial purity of anatabine base with BHT was 94.87%. Anatabine stability, with and without BHT is reported in Table 4

TABLE 4

| Day | Storage Temperature | Purity (%) (with BHT) | Purity (%) (without BHT) |
|---|---|---|---|
| 1 | 25-28° C. | 93.27 | 89.63 |
| | 2-8° C. | 93.26 | 94.44 |
| | −20° C. | 94.26 | 93.90 |
| 2 | 25-28° C. | 92.73 | 87.59 |
| | 2-8° C. | 94.83 | 94.05 |
| | −20° C. | 94.73 | 94.62 |
| 3 | 25-28° C. | 87.44 | 80.74 |
| | 2-8° C. | 94.26 | 91.65 |
| | −20° C. | 94.62 | 93.87 |
| 12 | 25-28° C. | 85.10 | 79.59 |
| | 2-8° C. | 94.18 | 90.12 |
| | −20° C. | 94.74 | 94.01 |

Example 6

Preparation of Anatabine Salts

To a solution of anatabine (4.0 g, 24.9 mmol) in acetone (20 ml), L-(+)-tartaric acid (3.37, 22.4 mmol) was added at room temperature. The reaction mass was warmed to 50° C. for 16 hours. The supernatant was decanted and the solid was triturated with diethyl ether (20 ml), filtered and dried under vacuum.

TABLE 5

| Solvent Used | Anatabine Tartrate (% Purity by HPLC) |
|---|---|
| Isopropyl alcohol | >94% |
| Acetone | >99% |

To a solution of anatabine (0.47 g, 2.9 mmol) in acetone (3 ml), citric acid (0.5 g, 2.6 mmol) was added at room temperature under a nitrogen atmosphere. The reaction mass was warmed to 50° C. for 16 hours. The supernatant was decanted and the solid was triturated with diethyl ether (20 ml), filtered and dried under vacuum.

TABLE 6

| Solvent Used | Anatabine Citrate (% Purity by HPLC) |
|---|---|
| Acetone | >97% |

Example 7

Reduced Caffeine Yerba Maté Extract

The Yerba maté extract is prepared by shredding Yerba maté materials and mixing with a water/ethanol (1/1 by volume) solution in a mixture of about four leaves per 10 ml of the water/ethanol mixture. The materials are then extracted overnight with continuous stirring. The solution is then removed from the Yerba maté residue and stored. The residue is then further extracted overnight two more times with the same volume of water/ethanol mixture, and the three extracts are combined and filtered to remove the particulate Yerba maté material. The combined extracts are subjected to removal of the water/ethanol by vacuum evaporation. The resultant extract is then weighed and solubilized in distilled water.

Example 8

Compositions are prepared by combining appropriate amounts of anatabine prepared synthetically as described in Examples 1-3 above and the Yerba maté extract of Example 7 to give the amounts of anatabine and Yerba maté indicated in Table 6 below, along with one or more pharmaceutically acceptable vehicles or carriers.

TABLE 6

| Example | Anatabine (mg) | Yerba Maté (mg caffeine equivalents) |
| --- | --- | --- |
| 8A | 0.1 | 60 |
| 8B | 0.2 | 80 |
| 8C | 0.2 | 100 |
| 8D | 0.2 | 140 |
| 8E | 0.2 | 160 |
| 8F | 0.2 | 180 |
| 8G | 0.2 | 200 |
| 8H | 0.2 | 220 |
| 8I | 0.2 | 240 |
| 8J | 0.3 | 60 |
| 8K | 0.3 | 80 |
| 8L | 0.3 | 100 |
| 8M | 0.3 | 140 |
| 8N | 0.3 | 160 |
| 8O | 0.3 | 180 |
| 8P | 0.3 | 200 |
| 8Q | 0.3 | 220 |
| 8R | 0.3 | 240 |
| 8S | 0.4 | 60 |
| 8T | 0.4 | 80 |
| 8U | 0.4 | 100 |
| 8V | 0.4 | 140 |
| 8W | 0.4 | 160 |
| 8X | 0.4 | 180 |
| 8Y | 0.4 | 200 |
| 8Z | 0.4 | 220 |
| 8AA | 0.4 | 240 |
| 8AB | 0.5 | 60 |
| 8AC | 0.5 | 80 |
| 8AD | 0.5 | 100 |
| 8AE | 0.5 | 140 |
| 8AF | 0.5 | 160 |
| 8AG | 0.5 | 180 |
| 8AH | 0.5 | 200 |
| 8AI | 0.5 | 220 |
| 8AJ | 0.5 | 240 |

Example 9

This example reports a randomized, double-blind, crossover, active-controlled study, comparing a lozenge containing approximately 0.1 mg anatabine and 18 mg (+/−5%) Yerba maté extract ("Product A"), to a smokeless tobacco product as described below ("Product B"). The anatabine content of Product A is similar to that expected to be ingested as a result of smoking cigarettes and is approximately the same magnitude as that in anatabine-rich foods. The Yerba maté content of Product A is equal to about one cup of Yerba maté herbal tea. The source of the anatabine polacrilex was Emerson Resources, Inc. (Norristown, Pa.) and the source of the Yerba maté extract was Wild Flavors, Inc. (Erlanger, Ky., USA), product code FAKP751.

While the invention has been described with respect to specific examples, those skilled in the art will appreciate that there are numerous variations and permutations of the above described systems and techniques that fall within the spirit and scope of the invention as set forth in the appended claims.

A compressed dissolvable smokeless tobacco lozenge ("Product B") was made from purified and filtered tobacco extract bound to polacrilex resin (Amberlite IRP64; Rohm and Haas). The product was compressed into a small lozenge which contains approximately 2 mg nicotine. The tobacco polacrilex lozenge was the same size, shape, and flavor as the anatabine/Yerba maté lozenge to maintain the blind.

Subjects were selected who met the following criteria:
(a) healthy male or female between 23-72 years old. (b) regular smoker who smokes 1+ pack of cigarettes per day for at least 5 years. (c) score equal to or greater than 6.0 on the Fagerstrom Nicotine Tolerance Scale. (d) have a general desire to quit smoking within 6 months.

Two studies of the temporary relief of the urge to smoke were conducted, measured by the QSU score (Questionnaire of Smoking Urges), a validated commonly used psychometric instrument. Cox L, Sanderson L, et. al., Evaluation of the Brief Questionnaire of Smoking Urges (QSU-brief) in Laboratory and Clinical Settings, Nicotine and Tobacco Research, 3:1, 7-18. The primary efficacy variable was the QSU. The QSU questionnaire was administered several times during the study day, before and after study product administration. Each question on the QSU was rated on a seven point scale from "strongly disagree (rating 1)" to "strongly agree (rating 7)." Summaries include the sample size, mean, median, standard deviation, minimum, and maximum. The treatment groups were compared using an Analysis of Variance (ANOVA). The model for the analysis included the factors of treatment sequence, subject, and treatment group.

The first study was a 49-patient, 4-way crossover (each patient had four sessions, one session for each of 4 treatments) testing a 4.0 mg smokeless tobacco product, a 4.0 mg NRT product and a corresponding flavor-only control. The second study was a 107-patient, two-way, crossover study of no treatment (No Product), Product A, and Product B. Since these were similar studies, using identical test methods and outcome variables, it was possible to pool the results. The pre- to post-score differences for each group were calculated, then divided by the pooled standard deviations to generate Effect Sizes (effect size is a general measure of the magnitude of an effect, obtained by dividing the change score by the pooled standard deviation of the scores, in units of SD).

The active controls in each study were then compared, and a conversion factor (ES Nicotine Study A/ES Nicotine Study B) calculated to correct for any potential different sensitivity between the studies. The Effect Sizes, corrected for interstudy differences, were then plotted. As can be seen in FIG. 1, Product B (Nicotine) had the strongest effect in reducing craving as measured by QSU. However, Product A (CigRx™) had about 60% of the nicotine effect, and about 1.5 times the flavor only effect. The flavor-only lozenges had a significant effect relative to the No Product control. These data demonstrate the utility and efficacy of the anatabine/Yerba maté composition in reducing the urge to smoke. Importantly, the composition of the present invention using low amounts of anatabine and Yerba maté provides an alternative to nicotine based smoking cessation therapies, thereby avoiding the disadvantages of ingesting nicotine, while also avoiding the disadvantages associated with ingesting high amounts of anatabine and/or Yerba maté. The compositions of the present invention also provide significantly reduced cravings compared to flavor-only lozenges. The compositions of the present invention thus provide an effective means of reducing the desire to smoke compared to a tobacco lozenge or nicotine replacement therapy for chronic smokers expressing a desire to have an alternative to cigarettes.

Figure 2:
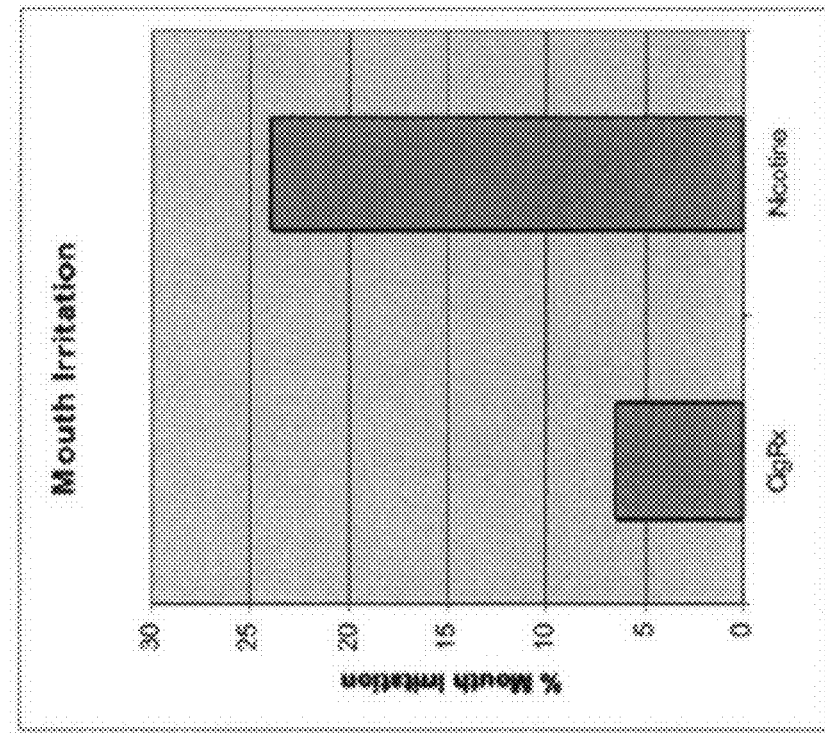
FIG. 2 is a graphical depiction of the results of subjects' mouth irritation upon administration of tobacco (Nicotine) and anatabine/Yerba maté (CigRx™)

As shown in FIG. 2, the subjects reported significantly lower occurrences of mouth irritation from Product A (~6%) relative to Product B (~24%). This is a significant improvement, since the ability of Product B to act as an alternative to a cigarette is particularly diminished for the nearly 1 in 4 subjects who reported mouth irritation from use of that product. Product A, for which reported instances of mouth irritation were only about 6%, thus provides a good alternative to the tobacco lozenge, especially for individuals who are prone to experience mouth irritation from nicotine.

Figure 3:
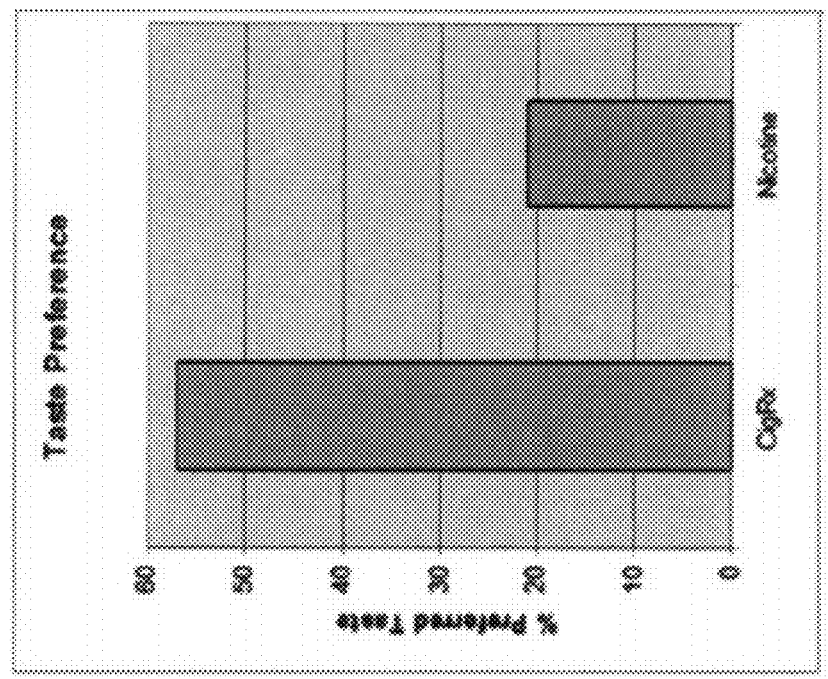
FIG. 3 is a graphical depiction of the results of subjects' taste preference between tobacco (Nicotine) and anatabine/Yerba maté (CigRx™)
Figure 4:
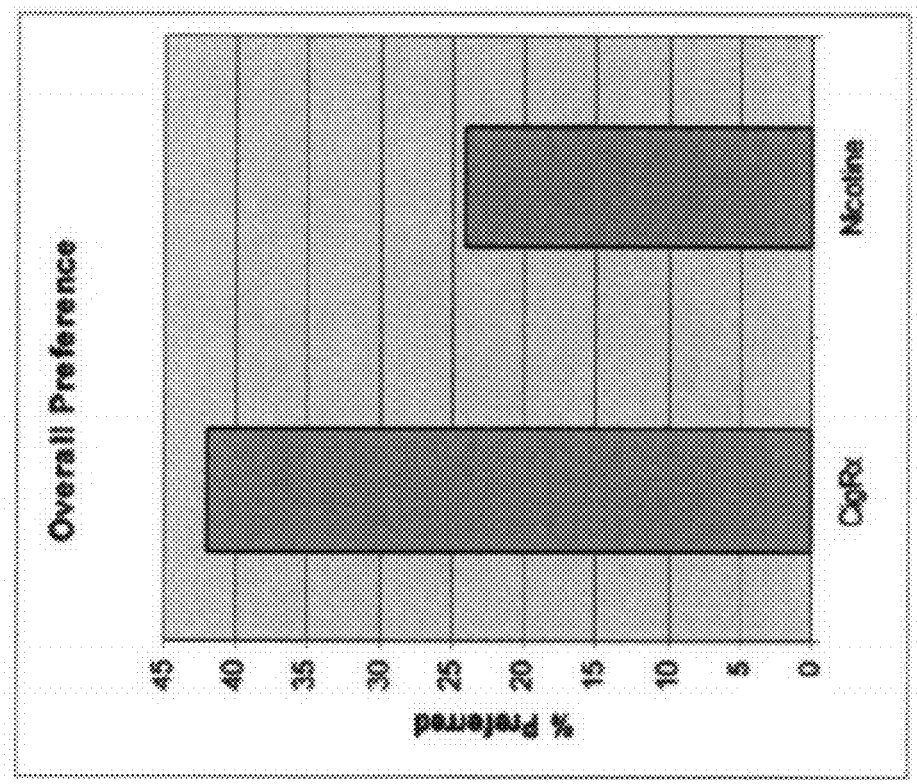
FIG. 4 is a graphical report of the results of subjects' overall preference between tobacco (Nicotine) and anatabine/Yerba maté (CigRx™).

As shown in FIG. 3, the subjects preferred the taste of Product A (~58%) by more than a 2:1 margin over that of Product B (~21%); and as shown in FIG. 4, the subjects reported an overall preference of Product A (~42%) to Product B (~24%) by a significant margin. Thus, in addition to having reduced occurrences of mouth irritation as described above, subjects found Product A to have a more pleasant taste and provide a better overall experience than that associated with the nicotine-containing Product B. By providing individuals with a more pleasant overall experience and reduced instances of undesirable side effects, the anatabine/Yerba maté composition of the present invention provides an effective and more desirable alternative to cigarettes.

What is claimed is:

1. A composition in dosage form comprising anatabine or a pharmaceutically acceptable or food grade salt thereof in an amount of from about 0.1 to about 0.5 mg per dosage form, a Yerba maté extract in an amount of from about 1 to about 100 mg per dosage form, and a pharmaceutically acceptable vehicle, diluent, or carrier.

2. The composition of claim 1, wherein the anatabine is synthetic anatabine or a pharmaceutically acceptable or food grade salt thereof.

3. The composition of claim 1 wherein anatabine is provided in the form of an extract of a plant selected from the group consisting of datura, mandrake, belladonna, capsicum, potato, nicotiana, eggplant, and petunia.

4. The composition of claim 1, wherein the dosage form is selected from the group consisting of a beverage, a chew, a tablet, a lozenge, and a gum.

5. A method of providing an alternative to cigarette smoking that reduces the desire to smoke comprising administering to a subject in need thereof the composition of claim 1.

6. The method of claim 5 wherein the subject is a human.

7. A method of treating at least one of smoking cessation, tobacco withdrawal symptoms, tobacco dependence, and weight loss in a subject comprising administering to a subject in need thereof the composition of claim 1.

8. The method of claim 7 wherein the subject is a human.

9. A nutraceutical composition in dosage form comprising anatabine or a pharmaceutically acceptable or food grade salt thereof in an amount of from about 0.1 to about 0.5 mg per dosage form, a Yerba maté extract in an amount of from about 1 to about 100 mg per dosage form, and a pharmaceutically acceptable vehicle, diluent, or carrier.

10. The nutraceutical composition of claim 9, wherein anatabine or a pharmaceutically acceptable or food grade salt thereof is present in an amount of from about 0.1 to about 0.3 mg per dosage form.

11. The nutraceutical composition of claim 9, wherein anatabine or a pharmaceutically acceptable or food grade salt thereof is present in an amount of or from about 0.1 to about 0.2 mg per dosage form.

12. The nutraceutical composition of claim 9, wherein the Yerba maté extract is present in an amount of from about 1 to about 50 mg per dosage form.

13. The nutraceutical composition of claim 9, wherein the dosage form is selected from the group consisting of a beverage, a chew, a tablet, a lozenge, and a gum.

14. The nutraceutical composition of claim 12, wherein the Yerba maté extract is present in an amount of from about 10 to about 25 mg per dosage form.

15. A method of temporarily reducing the desire to smoke, reducing nicotine cravings, or treating at least one of smoking cessation, tobacco withdrawal symptoms, tobacco dependence, and weight loss in a subject comprising administering to a subject in need thereof the nutraceutical composition of claim 9.

16. The method of claim 15 wherein the subject is a human.

17. A composition in dosage form comprising anatabine or a pharmaceutically acceptable or food grade salt thereof in an amount of from about 0.1 to about 0.5 mg per dosage form, a Yerba maté extract in dosage form, and a pharmaceutically acceptable vehicle, diluent, or carrier, wherein the Yerba maté extract and anatabine or salt thereof are present in a ratio of from 120:1 to 1200:1 (w/w).

18. The composition of claim 17, wherein the ratio is from 150:1 to 1000:1 (w/w).

19. The composition of claim 17, wherein the anatabine is synthetic anatabine or a pharmaceutically acceptable or food grade salt thereof 20. The composition of claim 17, wherein the dosage form is selected from the group consisting of a beverage, a chew, a tablet, a lozenge, and a gum.

* * * * *